United States Patent
Soltani et al.

(10) Patent No.: US 10,188,410 B2
(45) Date of Patent: Jan. 29, 2019

(54) POWER PARAMETERS FOR ULTRASONIC CATHETER

(75) Inventors: Azita Soltani, Snohomish, WA (US); Kim R. Volz, Duvall, WA (US)

(73) Assignee: EKOS CORPORATION, Bothell, WA (US)

( * ) Notice: Subject to any disclaimer, the term of this patent is extended or adjusted under 35 U.S.C. 154(b) by 2089 days.

(21) Appl. No.: 11/971,172

(22) Filed: Jan. 8, 2008

(65) Prior Publication Data

US 2008/0171965 A1   Jul. 17, 2008

Related U.S. Application Data

(60) Provisional application No. 60/884,010, filed on Jan. 8, 2007, provisional application No. 60/969,524, filed on Aug. 31, 2007.

(51) Int. Cl.
*A61B 17/22* (2006.01)
*A61B 17/00* (2006.01)

(52) U.S. Cl.
CPC .. *A61B 17/2202* (2013.01); *A61B 2017/0019* (2013.01); *A61B 2017/00181* (2013.01);
(Continued)

(58) Field of Classification Search
CPC .... A61M 2205/058; A61M 2205/3693; A61M 11/005; A61M 2037/007; A61M 37/0092; A61K 41/0023; A61K 41/0028; A61K 41/0033; A61F 9/00745; A61F 2250/0092; A61F 2250/0095; A61B 17/2204; A61B 17/2202; A61B 2017/22088; A61B 17/22012; A61B 17/22081; A61B 2017/22098; A61B 2017/0019; A61B 17/22004; A61N 2007/0004;
(Continued)

(56) References Cited

U.S. PATENT DOCUMENTS 3,352,303 A    11/1967   Delaney
3,430,625 A     3/1969   McLeod, Jr.
(Continued)

FOREIGN PATENT DOCUMENTS

EP   0 634 189 A2   1/1995
EP   0 670 147      2/1995
(Continued)

OTHER PUBLICATIONS

International Search Report Application No. PCT/US2008/050540.
(Continued)

*Primary Examiner* — Bhisma Mehta
*Assistant Examiner* — Laura Schell
(74) *Attorney, Agent, or Firm* — Knobbe, Martens, Olson & Bear LLP

(57) ABSTRACT

In one embodiment of the present invention, a method of applying ultrasonic energy to a treatment site within a patient's vasculature comprises positioning an ultrasound radiating member at a treatment site within a patient's vasculature. The method further comprises activating the ultrasound radiating member to produce pulses of ultrasonic energy at a cycle period T≤1 second. The acoustic parameters such as peak power, pulse width, pulse repetition frequency and frequency or any combination of them can be varied non-linearly.

7 Claims, 15 Drawing Sheets

(52) U.S. Cl.
CPC ............... *A61B 2017/00185* (2013.01); *A61B 2017/00194* (2013.01)

(58) Field of Classification Search
CPC .... A61N 2007/0043; A61N 2007/0047; A61N 2007/0052; A61N 2007/0073; A61N 7/022; A61N 2007/025
USPC ..................................................... 604/20, 22
See application file for complete search history.

(56) References Cited

U.S. PATENT DOCUMENTS

| | | |
|---|---|---|
| 3,437,851 A | 4/1969 | Cady |
| 3,433,226 A | 5/1969 | Knight |
| 3,565,062 A | 2/1971 | Kuris |
| 3,827,115 A | 8/1974 | Bom |
| 3,861,391 A | 1/1975 | Antonevich et al. |
| 3,902,083 A | 8/1975 | Zoltan |
| 3,941,122 A | 3/1976 | Jones |
| 4,192,294 A | 3/1980 | Gekhman et al. |
| 4,309,989 A | 1/1982 | Fahim |
| 4,319,580 A | 3/1982 | Colley |
| 4,354,502 A | 10/1982 | Colley et al. |
| 4,639,735 A | 1/1987 | Yamamoto et al. |
| 4,682,596 A | 7/1987 | Bales et al. |
| 4,692,139 A | 9/1987 | Stiles |
| 4,754,752 A | 7/1988 | Ginsburg et al. |
| 4,808,153 A | 2/1989 | Parisi |
| 4,821,740 A | 4/1989 | Tachibana et al. |
| 4,870,953 A | 10/1989 | Donmicheal et al. |
| 4,921,478 A | 5/1990 | Solano et al. |
| 4,936,281 A | 6/1990 | Stasz |
| 4,948,587 A | 8/1990 | Kost et al. |
| 4,953,565 A | 9/1990 | Tachibana et al. |
| 4,971,991 A | 11/1990 | Umemura et al. |
| 5,058,570 A | 10/1991 | Idemoto et al. |
| 5,069,664 A | 12/1991 | Guess |
| 5,076,276 A | 12/1991 | Sakurai et al. |
| 5,088,499 A | 2/1992 | Unger |
| 5,129,883 A | 7/1992 | Black |
| 5,158,071 A | 10/1992 | Umemura et al. |
| 5,163,421 A | 11/1992 | Bernstein et al. |
| 5,163,436 A | 11/1992 | Saitoh et al. |
| 5,197,946 A | 3/1993 | Tachibana |
| 5,267,954 A | 12/1993 | Nita |
| 5,267,985 A | 12/1993 | Shimada |
| 5,269,291 A | 12/1993 | Carter |
| 5,279,546 A | 1/1994 | Mische et al. |
| 5,304,115 A | 4/1994 | Pflueger |
| 5,307,816 A | 5/1994 | Hashimoto |
| 5,312,328 A | 5/1994 | Nita et al. |
| 5,315,998 A | 5/1994 | Tachibana et al. |
| 5,318,014 A | 6/1994 | Carter |
| 5,326,342 A | 7/1994 | Pflueger |
| 5,342,292 A | 8/1994 | Nita et al. |
| 5,344,395 A | 9/1994 | Whalen et al. |
| 5,345,940 A | 9/1994 | Seward |
| 5,362,309 A | 11/1994 | Carter |
| 5,368,557 A | 11/1994 | Nita et al. |
| 5,368,558 A | 11/1994 | Nita |
| 5,380,273 A | 1/1995 | Dubrul et al. |
| 5,401,237 A | 3/1995 | Tachibana et al. |
| 5,403,323 A | 4/1995 | Smith |
| 5,405,322 A | 4/1995 | Lennox et al. |
| 5,423,797 A | 6/1995 | Adrian et al. |
| 5,431,663 A | 7/1995 | Carter |
| 5,440,914 A | 8/1995 | Tachibana et al. |
| 5,447,509 A * | 9/1995 | Mills et al. ........................ 606/1 |
| 5,456,259 A | 10/1995 | Barlow et al. |
| 5,474,530 A | 12/1995 | Passafaro |
| 5,474,531 A | 12/1995 | Carter |
| 5,498,236 A | 3/1996 | Dubrul et al. |
| 5,509,896 A | 4/1996 | Carter |
| 5,523,058 A | 6/1996 | Umemura |
| 5,524,624 A | 6/1996 | Tepper et al. |
| 5,542,917 A | 8/1996 | Nita et al. |
| 5,542,935 A | 8/1996 | Unger et al. |
| 5,558,092 A | 9/1996 | Unger et al. |
| 5,582,586 A | 12/1996 | Tachibana et al. |
| 5,603,327 A | 2/1997 | Eberle |
| 5,606,974 A | 3/1997 | Castellano |
| 5,618,275 A | 4/1997 | Bock |
| 5,620,409 A | 4/1997 | Gans et al. |
| 5,620,479 A | 4/1997 | Diederich |
| 5,624,382 A | 4/1997 | Oppelt et al. |
| 5,628,728 A | 5/1997 | Tachibana et al. |
| 5,630,837 A | 5/1997 | Crowley |
| 5,648,098 A | 7/1997 | Porter |
| 5,660,909 A | 8/1997 | Tachibana et al. |
| 5,681,296 A | 10/1997 | Ishida |
| 5,694,936 A | 12/1997 | Fujimoto |
| 5,695,460 A | 12/1997 | Siegel et al. |
| 5,720,710 A * | 2/1998 | Tachibana et al. ............... 601/2 |
| 5,724,976 A | 3/1998 | Hirama et al. |
| 5,725,494 A | 3/1998 | Brisken |
| 5,728,062 A | 3/1998 | Brisken |
| 5,735,811 A | 4/1998 | Brisken |
| 5,752,930 A | 5/1998 | Baudino et al. |
| 5,775,338 A | 7/1998 | Hastings |
| 5,823,962 A | 10/1998 | Lerch et al. |
| 5,827,203 A | 10/1998 | Nita |
| 5,834,880 A | 11/1998 | Lewandowski et al. |
| 5,836,896 A | 11/1998 | Rosenschein |
| 5,836,940 A | 11/1998 | Gregory |
| 5,840,031 A | 11/1998 | Crowley |
| 5,846,218 A | 12/1998 | Brisken et al. |
| 5,876,345 A | 3/1999 | Eaton et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,934,284 A | 8/1999 | Plaia et al. |
| 5,957,851 A | 9/1999 | Hossack |
| 5,957,882 A | 9/1999 | Nita et al. |
| 5,971,949 A | 10/1999 | Levin et al. |
| 5,976,120 A | 11/1999 | Chow et al. |
| 5,997,497 A | 12/1999 | Nita et al. |
| 6,001,069 A * | 12/1999 | Tachibana ........ A61B 17/22012 601/2 |
| 6,024,718 A | 2/2000 | Chen et al. |
| 6,033,397 A | 3/2000 | Laufer et al. |
| 6,063,069 A | 5/2000 | Cragg et al. |
| 6,066,123 A | 5/2000 | Bednarski et al. |
| 6,088,613 A | 7/2000 | Unger |
| 6,089,573 A | 7/2000 | Udagawa |
| 6,096,000 A | 8/2000 | Tachibana et al. |
| 6,113,558 A | 9/2000 | Rosenschein et al. |
| 6,113,570 A | 9/2000 | Siegel et al. |
| 6,117,101 A | 9/2000 | Diedrich et al. |
| 6,135,976 A | 10/2000 | Tachibana et al. |
| 6,149,596 A | 11/2000 | Bancroft |
| 6,176,842 B1 | 1/2001 | Tachibana et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,287,271 B1 | 9/2001 | Dubrul et al. |
| 6,296,619 B1 | 10/2001 | Brisken et al. |
| 6,298,264 B1 | 10/2001 | Zhong et al. |
| 6,299,597 B1 | 10/2001 | Buscemi et al. |
| 6,312,402 B1 | 11/2001 | Hansmann |
| 6,319,220 B1 * | 11/2001 | Bylsma ............... A61F 9/00745 604/22 |
| 6,361,554 B1 | 3/2002 | Brisken |
| 6,391,042 B1 | 5/2002 | Cimino |
| 6,394,956 B1 | 5/2002 | Chandrasekaran et al. |
| 6,398,772 B1 | 6/2002 | Bond et al. |
| 6,398,792 B1 | 6/2002 | O'Connor |
| 6,416,740 B1 | 7/2002 | Unger |

(56) References Cited

U.S. PATENT DOCUMENTS

| | | | |
|---|---|---|---|
| 6,454,737 B1 | 9/2002 | Nita et al. |
| 6,454,757 B1 | 9/2002 | Nita et al. |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,494,891 B1 | 12/2002 | Cornish et al. |
| 6,506,584 B1 | 1/2003 | Chandler et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,544,259 B1 | 4/2003 | Tsaliovich |
| 6,551,337 B1 | 4/2003 | Rabiner et al. |
| 6,558,366 B1 | 5/2003 | Drasler et al. |
| 6,562,021 B1 | 5/2003 | Derbin et al. |
| 6,565,552 B1 | 5/2003 | Barbut |
| 6,575,956 B1 | 6/2003 | Brisken et al. |
| 6,579,277 B1 | 6/2003 | Rabiner et al. |
| 6,582,392 B1 | 6/2003 | Bennett et al. |
| 6,589,253 B1 | 7/2003 | Cornish et al. |
| 6,605,084 B2 | 8/2003 | Acker et al. |
| 6,623,444 B2 | 9/2003 | Babaev |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,723,063 B1 | 4/2004 | Zhang et al. |
| 6,723,064 B2 | 4/2004 | Babaev |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,767,345 B2 | 6/2004 | St. Germain et al. |
| 6,794,369 B2 | 9/2004 | Newman et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,905,505 B2 | 6/2005 | Dodson, Jr. et al. |
| 6,921,371 B2 | 7/2005 | Wilson |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver et al. |
| 6,979,293 B2 | 12/2005 | Hansmann et al. |
| 6,985,771 B2 | 1/2006 | Fischell et al. |
| 7,137,963 B2 | 11/2006 | Nita et al. |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,264,597 B2 | 9/2007 | Cathignol |
| 7,309,334 B2 | 12/2007 | von Hoffmann |
| 7,335,180 B2 | 2/2008 | Nita et al. |
| 7,341,569 B2 | 3/2008 | Soltani et al. |
| 7,344,509 B2 | 3/2008 | Hynynen et al. |
| 7,384,407 B2 | 6/2008 | Rodriguez et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,727,178 B2 | 6/2010 | Wilson et al. |
| 7,758,509 B2 | 7/2010 | Angelsen et al. |
| 7,771,372 B2 | 8/2010 | Wilson |
| 7,774,933 B2 | 8/2010 | Wilson et al. |
| 7,789,830 B2 | 9/2010 | Fujita et al. |
| 7,818,854 B2 | 10/2010 | Wilson |
| 7,828,754 B2 | 11/2010 | Abe et al. |
| 7,828,762 B2 | 11/2010 | Wilson |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 8,167,831 B2 | 5/2012 | Wilson |
| 8,192,363 B2 | 6/2012 | Soltani et al. |
| 8,192,391 B2 | 6/2012 | Soltani |
| 8,226,629 B1 | 7/2012 | Keilman et al. |
| 8,696,612 B2 | 4/2014 | Wilson et al. |
| 8,740,835 B2 | 6/2014 | Soltani et al. |
| 8,852,166 B1 | 10/2014 | Keilman et al. |
| 9,044,568 B2 | 6/2015 | Wilcox et al. |
| 9,107,590 B2 | 8/2015 | Hansmann et al. |
| 9,192,566 B2 | 11/2015 | Soltani et al. |
| 9,849,273 B2 | 12/2017 | Soltani et al. |
| 9,943,675 B1 | 4/2018 | Keilman et al. |
| 2001/0007940 A1* | 7/2001 | Tu et al. ................... 606/41 |
| 2002/0032394 A1 | 5/2002 | Brisken et al. |
| 2002/0052620 A1 | 5/2002 | Barbut |
| 2002/0055731 A1 | 5/2002 | Atala et al. |
| 2002/0045890 A1 | 6/2002 | Celliers et al. |
| 2002/0082238 A1 | 6/2002 | Newman et al. |
| 2002/0068869 A1 | 8/2002 | Brisken et al. |
| 2002/0123787 A1 | 9/2002 | Weiss |
| 2002/0133111 A1 | 9/2002 | Shadduck |
| 2002/0077550 A1 | 10/2002 | Rabiner et al. |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0083608 A1 | 5/2003 | Evans et al. |
| 2003/0069525 A1 | 8/2003 | Brisken et al. |
| 2003/0163147 A1 | 8/2003 | Hare et al. |
| 2003/0220568 A1 | 11/2003 | Hansmann et al. |
| 2003/0233085 A1 | 12/2003 | Giammarusti |
| 2003/0236539 A1 | 12/2003 | Rabiner et al. |
| 2004/0001809 A1 | 1/2004 | Brisken et al. |
| 2004/0039311 A1 | 2/2004 | Nita et al. |
| 2004/0019318 A1 | 3/2004 | Wilson et al. |
| 2004/0024347 A1 | 3/2004 | Wilson et al. |
| 2004/0024393 A1 | 3/2004 | Nita et al. |
| 2004/0049148 A1 | 3/2004 | Rodriguez et al. |
| 2004/0059313 A1 | 3/2004 | Anderson et al. |
| 2004/0097996 A1 | 5/2004 | Hare et al. |
| 2004/0068189 A1 | 7/2004 | Wilson et al. |
| 2004/0138570 A1 | 7/2004 | Nita et al. |
| 2004/0162571 A1 | 8/2004 | Rabiner et al. |
| 2004/0171970 A1 | 9/2004 | Schleuniger |
| 2004/0171981 A1 | 9/2004 | Buffen et al. |
| 2004/0199228 A1 | 10/2004 | Wilson |
| 2004/0210134 A1 | 10/2004 | Hynynen et al. |
| 2004/0220514 A1 | 11/2004 | Cafferata |
| 2004/0236350 A1 | 11/2004 | Bolduc et al. |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043726 A1* | 2/2005 | McHale et al. ............ 606/27 |
| 2005/0054971 A1 | 3/2005 | Steen et al. |
| 2005/0065461 A1 | 3/2005 | Redding, Jr. |
| 2005/0043629 A1 | 5/2005 | Rabiner et al. |
| 2005/0043753 A1 | 5/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |

(56) References Cited

U.S. PATENT DOCUMENTS

| | | |
|---|---|---|
| 2005/0215946 A1 | 9/2005 | Hansmann et al. |
| 2005/0216044 A1 | 9/2005 | Hong |
| 2005/0096669 A1 | 10/2005 | Rabiner et al. |
| 2005/0249667 A1 | 11/2005 | Tuszynski |
| 2005/0256410 A1 | 11/2005 | Rabiner et al. |
| 2005/0113688 A1 | 12/2005 | Nita et al. |
| 2005/0119679 A1 | 12/2005 | Rabiner et al. |
| 2005/0277869 A1* | 12/2005 | Boukhny .................. 604/22 |
| 2006/0069303 A1 | 3/2006 | Couvillon |
| 2006/0106308 A1 | 5/2006 | Hansmann et al. |
| 2006/0173387 A1 | 8/2006 | Hansmann et al. |
| 2006/0184070 A1 | 8/2006 | Hansmann et al. |
| 2006/0241524 A1* | 10/2006 | Lee .................. A61M 37/0092 601/2 |
| 2006/0264809 A1 | 11/2006 | Hansmann et al. |
| 2007/0037119 A1 | 2/2007 | Pal et al. |
| 2007/0038158 A1 | 2/2007 | Nita et al. |
| 2007/0066978 A1 | 3/2007 | Schafer et al. |
| 2007/0129761 A1 | 6/2007 | Demarais et al. |
| 2007/0225619 A1 | 9/2007 | Rabiner et al. |
| 2007/0239027 A1 | 10/2007 | Nita |
| 2007/0249969 A1 | 10/2007 | Shields |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 9/2008 | Abrahamson et al. |
| 2008/0306499 A1 | 12/2008 | Katoh et al. |
| 2008/0315720 A1 | 12/2008 | Ma et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0112150 A1 | 4/2009 | Unger et al. |
| 2009/0187137 A1 | 7/2009 | Volz et al. |
| 2009/0209900 A1 | 8/2009 | Carmeli et al. |
| 2009/0216246 A1 | 8/2009 | Nita et al. |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0280505 A1 | 11/2010 | Mattiuzzi |
| 2010/0292685 A1 | 11/2010 | Katoh et al. |
| 2011/0004105 A1 | 1/2011 | Soltani et al. |
| 2011/0160621 A1 | 6/2011 | Nita |
| 2011/0288449 A1 | 11/2011 | Schenkengel |
| 2011/0301506 A1 | 12/2011 | Volz |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0179073 A1 | 7/2012 | Nita |
| 2012/0197277 A1 | 8/2012 | Stinis |
| 2012/0271203 A1 | 10/2012 | Soltani et al. |

FOREIGN PATENT DOCUMENTS

| | | |
|---|---|---|
| EP | 0744189 | 11/1996 |
| EP | 1090658 | 4/2001 |
| JP | 58-056869 | 4/1983 |
| JP | 59-063783 | 4/1984 |
| JP | 59-108378 | 6/1984 |
| JP | 61-244079 | 10/1986 |
| WO | WO/95/09572 | 4/1995 |
| WO | WO95/09572 | 4/1995 |
| WO | WO96/27341 | 9/1996 |
| WO | WO96/29935 | 10/1996 |
| WO | WO96/36286 | 11/1996 |
| WO | WO98/18391 | 5/1998 |
| WO | WO98/48711 | 11/1998 |
| WO | WO99/33500 | 7/1999 |
| WO | WO99/39647 | 8/1999 |
| WO | WO 99/044512 | 9/1999 |
| WO | WO00/38580 | 7/2000 |
| WO | WO01/95788 | 12/2001 |
| WO | WO02/13678 | 2/2002 |
| WO | WO02/15803 | 2/2002 |
| WO | WO02/15804 | 2/2002 |
| WO | WO03/051208 | 6/2003 |
| WO | WO 03/099382 | 12/2003 |
| WO | WO05/027756 | 3/2005 |
| WO | WO05/084552 | 9/2005 |
| WO | WO05/084553 | 9/2005 |
| WO | WO 2008/086372 | 7/2008 |
| WO | WO 2009/018472 | 2/2009 |
| WO | WO2009/079415 | 6/2009 |
| WO | WO2010/003130 | 1/2010 |
| WO | WO2011/003031 | 1/2011 |

OTHER PUBLICATIONS

European Patent Office; Office Action dated May 7, 2010, from related European Patent Application No. 08705775.8-2305.

European Patent Office; Office Action dated Nov. 29, 2010, from related European Patent Application No. 08705775.8-2305.

European Patent Office; Office Action dated Apr. 11, 2011, from related European Patent Application No. 08705775.8-2305.

International Searching Authority; Notification of Transmittal of the International Search Report and the Written Opinion of the International Searching Authority, or the Declaration; International Search Report; and Written Opinion of the International Searching Authority of PCT Application No. PCT/US2010/040834, Filing Date: Jul. 1, 2010; dated Sep. 23, 2010.

International Searching Authority; International Search Report and Publication of PCT Application No. PCT/US2008/050540, Filing Date: Jan. 8, 2008, Publication No. WO2008/086372, Publication Date: Jul. 17, 2008; dated Apr. 25, 2008.

International Searching Authority; International Preliminary Report on Patentability; and Written Opinion of the International Searching Authority of PCT Application No. PCT/US2008/050540, Filing Date: Jan. 8, 2008; dated Jul. 14, 2009.

International Searching Authority; Written Opinion of the International Searching Authority of PCT Application No. PCT/US2009/049634, Filing Date: Jul. 2, 2009; dated Feb. 2, 2010.

International Searching Authority; International Search Report of PCT Application No. PCT/US2009/049634, Filing Date: Jul. 2, 2009; dated Feb. 2, 2010.

USPTO; Office Action dated May 27, 2011, from related application U.S. Appl. No. 12/830,145, filed Jul. 2, 2010.

European Patent Office; Office Action dated Mar. 13, 2012, from related European Patent Application No. 08705775.8-2305.

Saletes et al., Effectiveness of Thrombolysis in Excitation Bifrequentielle Purely UT. Lyon, Apr. 12-16, 2010.

AIP Conference Proceedings. "Cavitation Generated by Amplitude Modulated HIFU: Investigation of the Intertial Caviation Threshold". May 5, 2010 http://scitation.aip.org/getabs/servlet/GetabsServlet?prog=normal&id=APCPCS000911000010001.

European Office Action dated Oct. 11, 2012 corresponding to European Application No. 08 705 775.8.

(56) References Cited

OTHER PUBLICATIONS

Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.
International Preliminary Report on Patentability in Application No. PCT/US2009/049634, dated Jan. 5, 2011.
Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.
Official Communication in European Application No. 08705775.8, dated Mar. 6, 2013.
Abbas, "Development of a Low Cost Shock Pressure Sensor", Thesis, Ohio University, College of Engineering and Technology, Mar. 1988, pp. 149.
Official Communication in European Application No. 12003010.1, dated Oct. 25, 2016.
European Extended Search Report dated Jan. 21, 2013 corresponding to European Application No. 12003010.1.
European Office Action dated Apr. 29, 2013 corresponding to European Application No. 09 774 579.8.
Extended European Search Report dated Sep. 11, 2012 corresponding to European Application No. 09774579.8.

\* cited by examiner

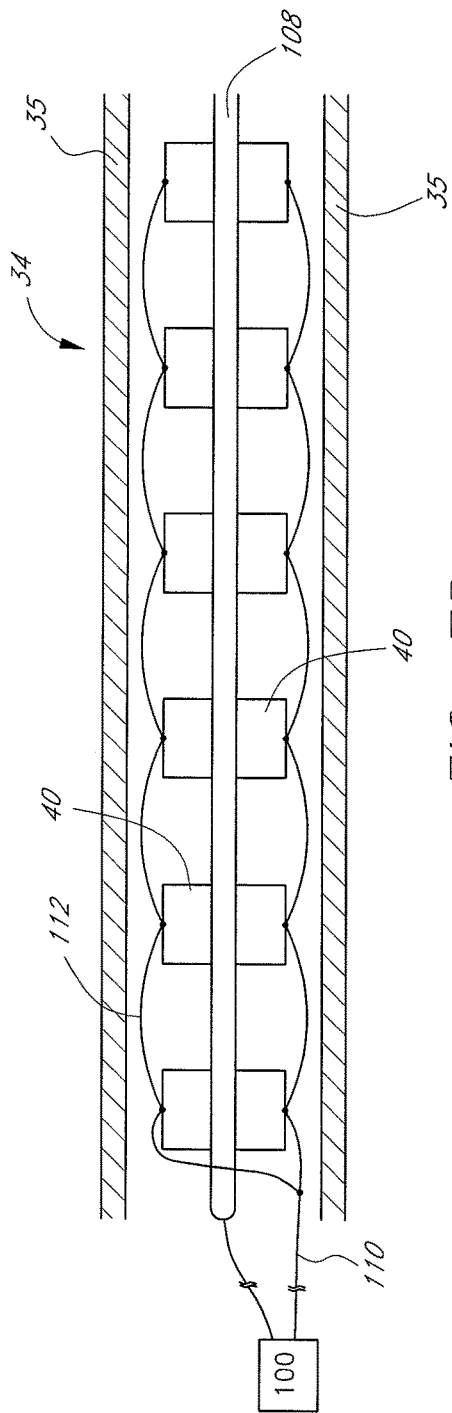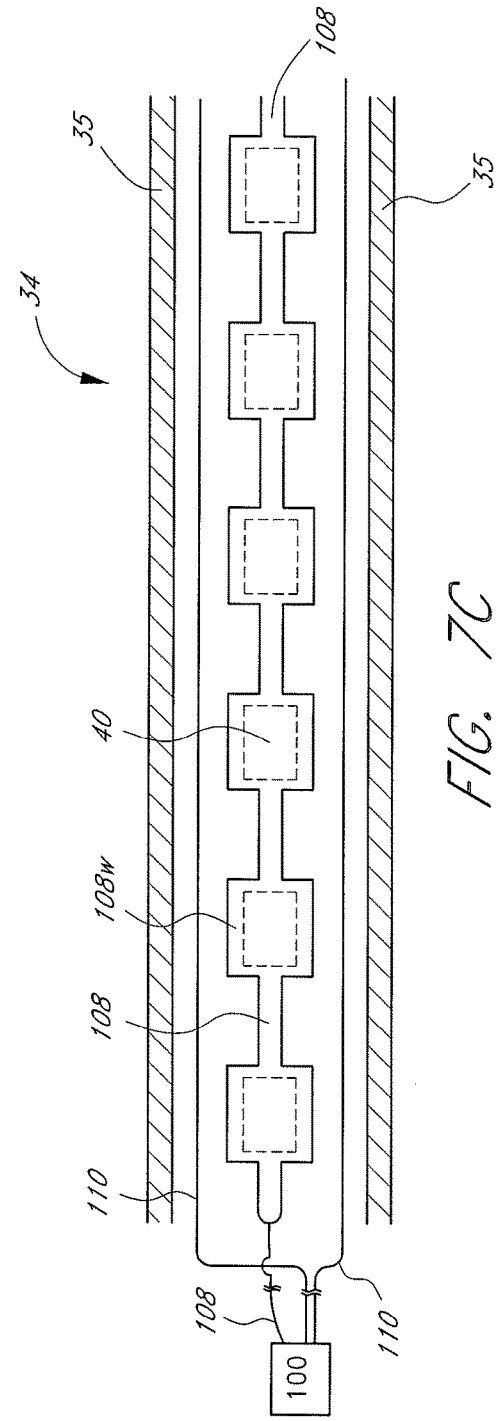

POWER PARAMETERS FOR ULTRASONIC CATHETER

PRIORITY INFORMATION

This application claims the priority benefit of U.S. Provisional Application No. 60/884,010 filed Jan. 8, 2007 and U.S. Provisional Application No. 60/969,524 filed Aug. 31, 2007, the entire contents of which are hereby incorporated by reference herein.

FIELD OF THE INVENTION

The present invention relates generally to ultrasound systems, and more specifically to ultrasound catheter systems.

BACKGROUND OF THE INVENTION

Ultrasonic energy had been used to enhance the intravascular delivery and/or effect of various therapeutic compounds. In one system, ultrasound catheters are used to deliver ultrasonic energy and therapeutic compounds to a treatment site within a patient's vasculature. Such ultrasound catheters can comprise an elongate member configured to be advanced through a patient's vasculature and an ultrasound assembly that is positioned near a distal end portion of the elongate member. The ultrasound assembly is configured to emit ultrasonic energy. Such ultrasound catheters can include a fluid delivery lumen that is used to deliver the therapeutic compound to the treatment site. In this manner, ultrasonic energy is delivered to the treatment site to enhance the effect and/or delivery of the therapeutic compound.

For example, ultrasound catheters have been successfully used to treat human blood vessels that have become occluded by plaque, thrombi, emboli or other substances that reduce the blood carrying capacity of the vessel. See, for example, U.S. Pat. No. 6,001,069. To remove the occlusion, the ultrasound catheter is advanced through the patient's vasculature to deliver a therapeutic compound containing dissolution compounds directly to the occlusion. To enhance the effect and/or delivery of the therapeutic compound, ultrasonic energy is emitted into the therapeutic compound and/or the surrounding tissue at the treatment site. In other applications, ultrasound catheters are used for other purposes, such as for the delivery and activation of light activated drugs. See, for example, U.S. Pat. No. 6,176,842.

SUMMARY OF THE INVENTION

While such ultrasound catheters systems have been proven to be successful, there is a general need to continue to improve the effectiveness and speed of such systems. In this manner, treatment and/or hospital time can be reduced.

Accordingly, one aspect of the present invention comprises an ultrasound catheter system comprising a catheter having at least ultrasonic element; a control system configured to generate power parameters to drive the ultrasonic element to generate ultrasonic energy. The control system is configured to vary non-linearly at least one of the power parameters.

Another aspect of the present invention comprises a method of operating an ultrasonic catheter. In the method, a catheter with at least one ultrasonic element is advanced to a treatment site in a patient's vascular system. The at least one ultrasonic element is driven to generate ultrasonic energy. A therapeutic compound is delivered to the treatment site through the catheter. The driving parameters of the ultrasonic element are non-linearly varied to attain non-linear acoustic output.

Another aspect of the present invention is a control system for an ultrasound catheter. The control system includes control unit configured to non-linearly vary acoustic parameters of an ultrasonic element of an ultrasonic catheter.

BRIEF DESCRIPTION OF THE DRAWINGS

Exemplary embodiments of the cavitation promoting systems and methods disclosed herein are illustrated in the accompanying drawings, which are for illustrative purposes only. The drawings comprise the following figures, in which like numerals indicate like parts.

FIG. 7B is a cross-sectional view of the ultrasound assembly of FIG. 7A taken along line 7B-7B.

FIG. 7C is a cross-sectional view of the ultrasound assembly of FIG. 7A taken along line 7C-7C.

DETAILED DESCRIPTION OF THE PREFERRED EMBODIMENTS

Figure 1:
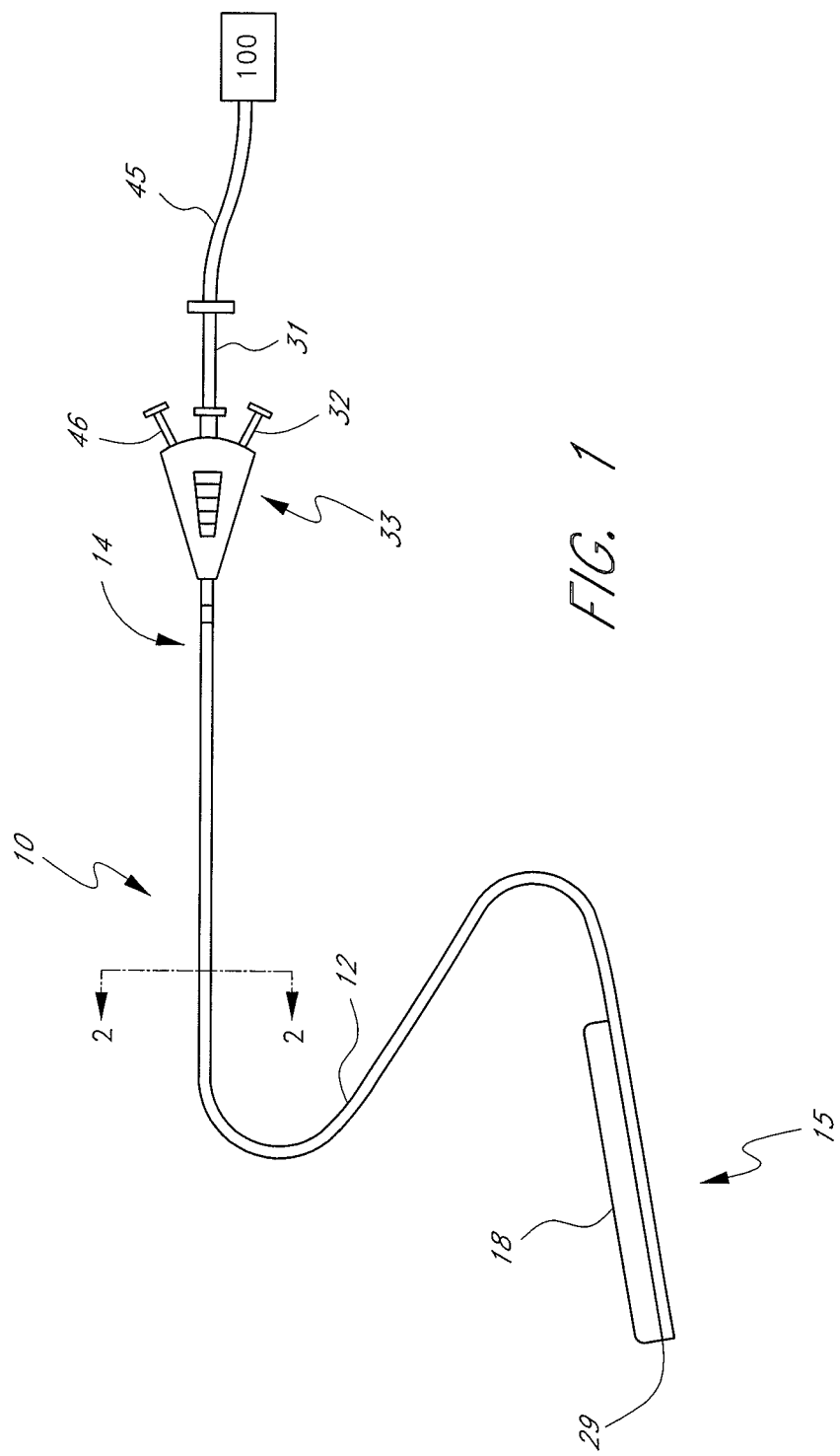
FIG. 1 is a schematic illustration of certain features of an example ultrasonic catheter.

As used herein, the term "ultrasonic energy" is used broadly, includes its ordinary meaning, and further includes mechanical energy transferred through pressure or compression waves with a frequency greater than about 20 kHz. Ultrasonic energy waves have a frequency between about 500 kHz and about 20 MHz in one example embodiment, between about 1 MHz and about 3 MHz in another example embodiment, of about 3 MHz in another example embodiment, and of about 2 MHz in another example embodiment. As used herein, the term "catheter" is used broadly, includes its ordinary meaning, and further includes an elongate flexible tube configured to be inserted into the body of a patient, such as into a body part, cavity, duct or vessel. As used herein, the term "therapeutic compound" is used broadly, includes its ordinary meaning, and encompasses drugs, medicaments, dissolution compounds, genetic materials, and other substances capable of effecting physiological functions. A mixture comprising such substances is encompassed within this definition of "therapeutic compound". As used herein, the term "end" is used broadly, includes its ordinary meaning, and further encompasses a region generally, such that "proximal end" includes "proximal region", and "distal end" includes "distal region".

As expounded herein, ultrasonic energy is often used to enhance the delivery and/or effect of a therapeutic compound. For example, in the context of treating vascular occlusions, ultrasonic energy has been shown to increase enzyme mediated thrombolysis by enhancing the delivery of thrombolytic agents into a thrombus, where such agents lyse the thrombus by degrading the fibrin that forms the thrombus. The thrombolytic activity of the agent is enhanced in the presence of ultrasonic energy in the thrombus. However, it should be appreciated that the invention should not be limited to the mechanism by which the ultrasound enhances treatment unless otherwise stated. In other applications, ultrasonic energy has also been shown to enhance transfection of gene-based drugs into cells, and augment transfer of chemotherapeutic drugs into tumor cells. Ultrasonic energy delivered from within a patient's body has been found to be capable of producing non-thermal effects that increase biological tissue permeability to therapeutic compounds by up to or greater than an order of magnitude.

Use of an ultrasound catheter to deliver ultrasonic energy and a therapeutic compound directly to the treatment site mediates or overcomes many of the disadvantages associated with systemic drug delivery, such as low efficiency, high therapeutic compound use rates, and significant side effects caused by high doses. Local therapeutic compound delivery has been found to be particularly advantageous in the context of thrombolytic therapy, chemotherapy, radiation therapy, and gene therapy, as well as in applications calling for the delivery of proteins and/or therapeutic humanized antibodies. However, it should be appreciated that in certain arrangements the ultrasound catheter can also be used in combination with systemic drug delivery instead or in addition to local drug deliver. In addition, local drug delivery can be accomplished through the use of a separate device (e.g., catheter).

As will be described below, the ultrasound catheter can include one or more one or more ultrasound radiating members positioned therein. Such ultrasound radiating members can comprise a transducer (e.g., a PZT transducer), which is configured to convert electrically energy into ultrasonic energy. In such embodiments, the PZT transducer is excited by specific electrical parameters (herein "power parameters" that cause it to vibrate in a way that generates ultrasonic energy). As will be explained below, Applicants have discovered that by non-linearly (e.g., randomly or pseudo randomly) varying one or more of the power parameters the effectiveness of the ultrasound catheter (e.g., the effectiveness of enhancing the removal of a thrombus) can be significantly enhanced. While, for example, U.S. Pat. No. 5,720,710 taught that randomly changing the frequency of the ultrasonic frequency could significantly enhance the remedial effect of the ultrasonic energy, these results with respect to varying the other acoustic parameters were not expected. In addition, because PZT transducers are often configured to be driven a particularly frequency, varying the other acoustic parameters may have significant advantages over varying the frequency. In addition, varying the electrical parameters may also be used in combination with varying the frequency (e.g., in a manner taught by U.S. Pat. No. 5,720,710.

The techniques disclosed herein are compatible with a wide variety of ultrasound catheters, several examples of which are disclosed in USA Patent Application Publication US 2004/0024347 A1 (published 5 Feb. 2004; discloses catheters especially well-suited for use in the peripheral vasculature) and USA Patent Application Publication 2005/0215942 A1 (published 29 Sep. 2005; discloses catheters especially well-suited for use in the cerebral vasculature). Certain of the techniques disclosed herein are compatible with ultrasound catheters that would be unable to generate cavitation at an intravascular treatment site but for the use of such techniques.

With reference to the illustrated embodiments, FIG. 1 illustrates an ultrasonic catheter 10 configured for use in a patient's vasculature. For example, in certain applications the ultrasonic catheter 10 is used to treat long segment peripheral arterial occlusions, such as those in the vascular system of the leg, while in other applications the ultrasonic catheter 10 is used to treat occlusions in the small vessels of the neurovasculature or other portions of the body (e.g., other distal portions of the vascular system). Thus, the dimensions of the catheter 10 are adjusted based on the particular application for which the catheter 10 is to be used.

The ultrasonic catheter 10 generally comprises a multi-component, elongate flexible tubular body 12 having a proximal region 14 and a distal region 15. The tubular body 12 includes a flexible energy delivery section 18 located in the distal region 15 of the catheter 10. The tubular body 12 and other components of the catheter 10 are manufactured in accordance with a variety of techniques. Suitable materials and dimensions are selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 1800 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, in certain embodiments nickel titanium or stainless steel wires are placed along or incorporated into the tubular body 12 to reduce kinking.

The energy delivery section 18 of the tubular body 12 optionally comprises a material that (a) is thinner than the material comprising the proximal region 14 of the tubular body 12, or (b) has a greater acoustic transparency than the material comprising the proximal region 14 of the tubular body 12. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 is formed from the same material or a material of the same thickness as the proximal region 18.

One or more fluid delivery lumens are incorporated into the tubular body 12. For example, in one embodiment a central lumen passes through the tubular body 12. The central lumen extends through the length of the tubular body 12, and is coupled to a distal exit port 29 and a proximal access port 31. The proximal access port 31 forms part of the backend hub 33, which is attached to the proximal region 14 of the catheter 10. The backend hub 33 optionally further comprises cooling fluid fitting 46, which is hydraulically connected to a lumen within the tubular body 12. The backend hub 33 also optionally comprises a therapeutic compound inlet port 1320, which is hydraulically connected to a lumen within the tubular body 12. The therapeutic compound inlet port 32 is optionally also hydraulically coupled to a source of therapeutic compound via a hub such as a Luer fitting.

The catheter 100 is configured to have one or more ultrasound radiating members positioned therein. For example, in certain embodiments an ultrasound radiating member is fixed within the energy delivery section 18 of the tubular body, while in other embodiments a plurality of ultrasound radiating members are fixed to an assembly that is passed into the central lumen. In either case, the one or more ultrasound radiating members are electrically coupled to a control system 100 via cable 45. In one embodiment, the outer surface of the energy delivery 18 section can include an cavitation promoting surface configured to enhance/promote cavitation at the treatment site.

With reference to FIG. 2-10, an exemplary arrangement of the energy delivery section 18 and other portions of the catheter 10 described above. This arrangement is particularly well-suited for treatment of peripheral vascular occlusions.

Figure 2:
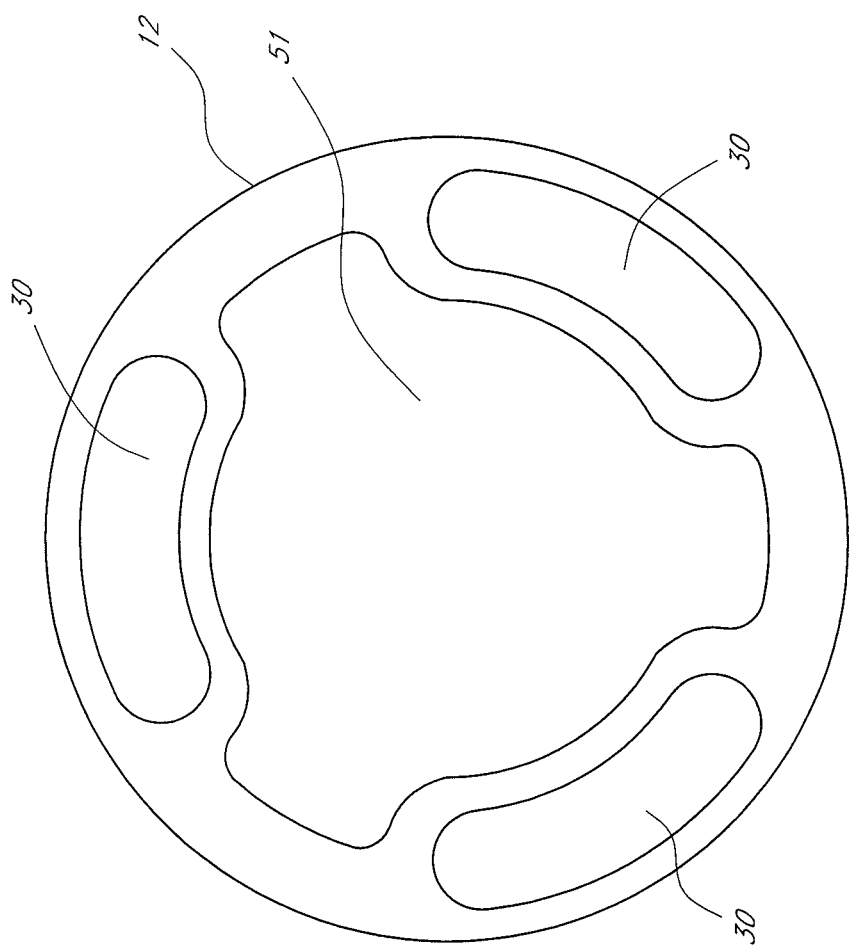
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
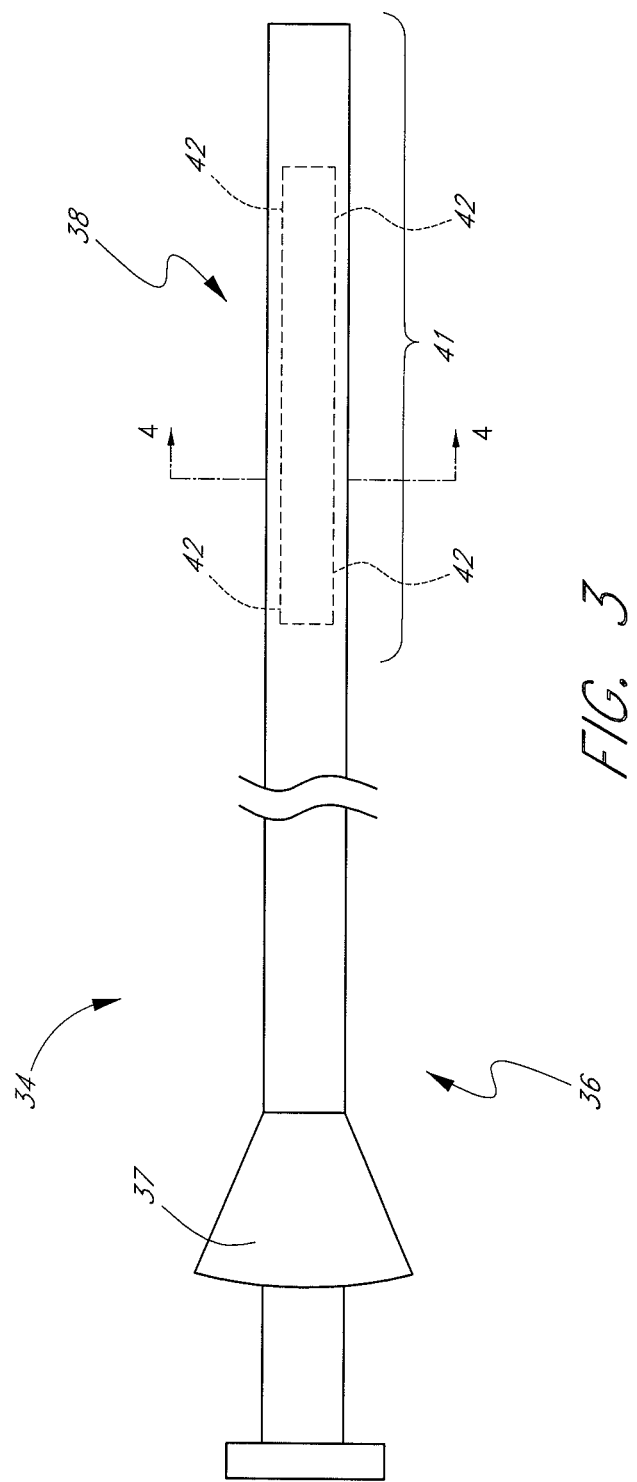
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members 40 form an ultrasound assembly 42, which will be described in detail below.

Figure 4:
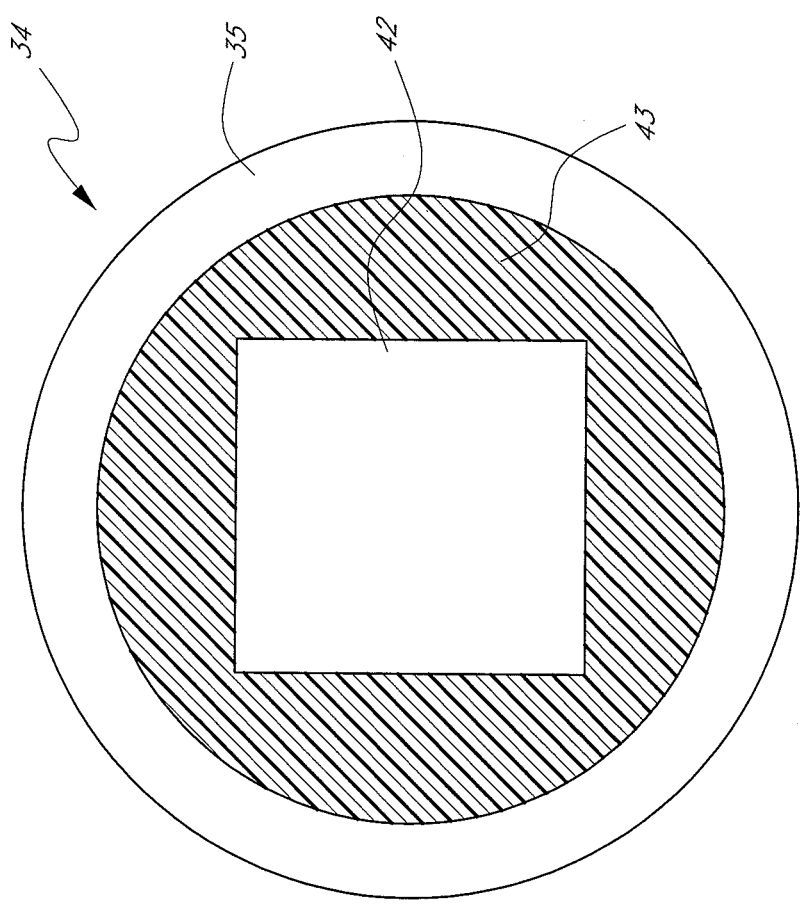
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
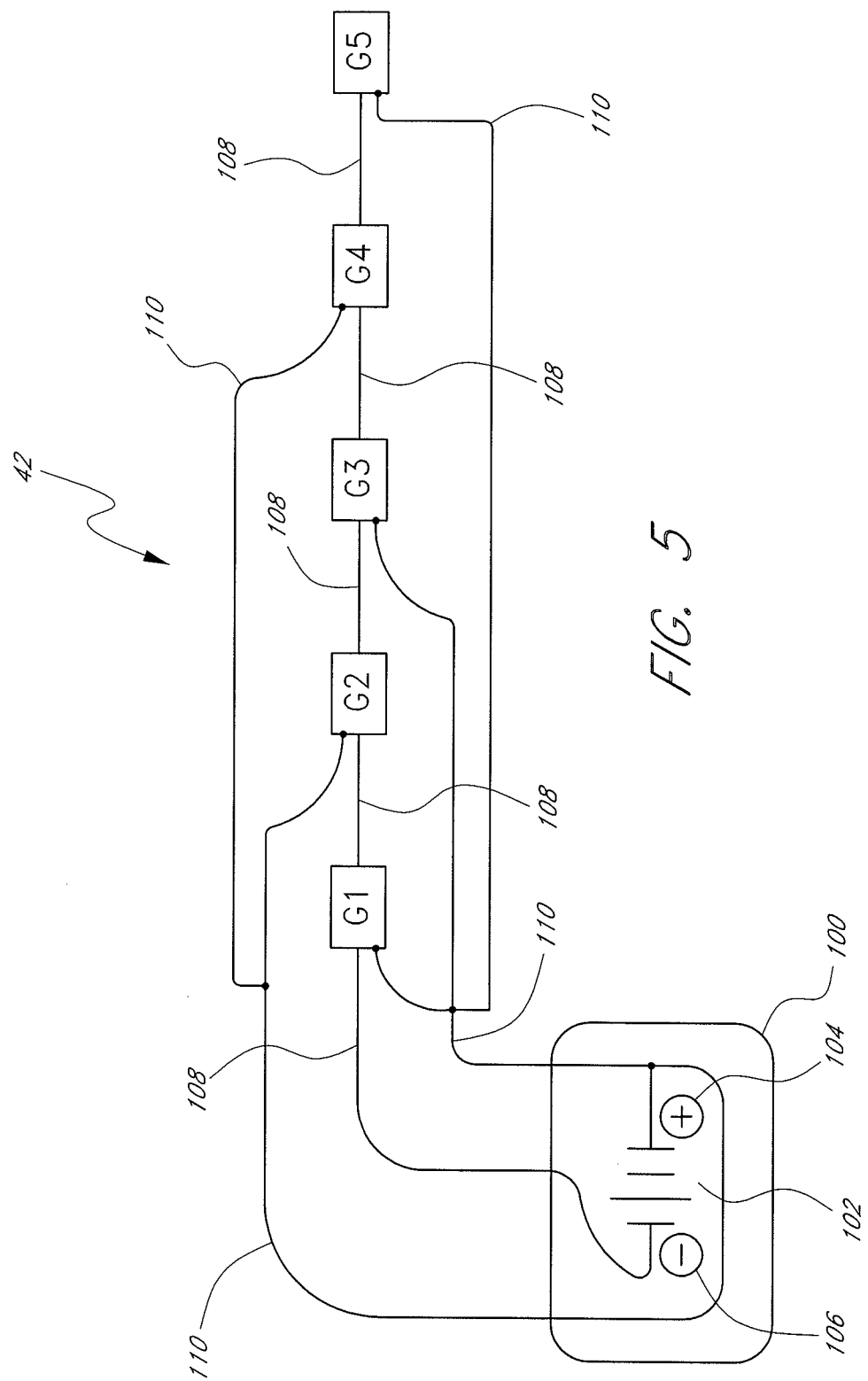
FIG. 5 is a schematic wiring diagram illustrating a preferred technique for electrically connecting five groups of ultrasound radiating members to form an ultrasound assembly.
Figure 6:
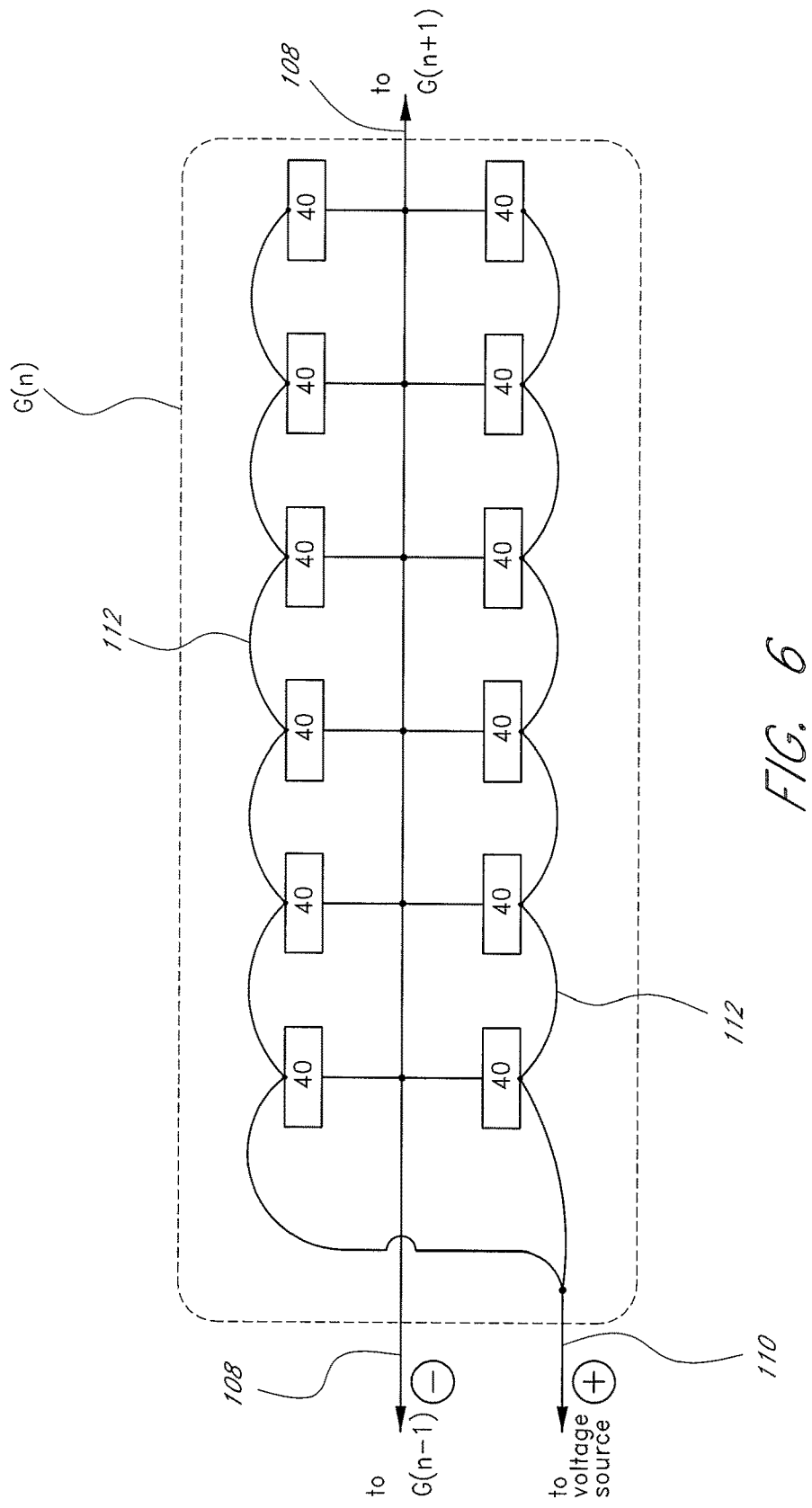
FIG. 6 is a schematic wiring diagram illustrating a preferred technique for electrically connecting one of the groups of FIG. 5.

In a preferred embodiment, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108. The control circuitry can be configured as part of the control system 1100 and can include circuits, control routines, controllers etc configured to vary one or more power parameters used to drive ultrasound radiating members 40, Referring now to FIG. 6, each group G1-G5 comprises a plurality of ultrasound radiating members 40. Each of the ultrasound radiating members 40 is electrically connected to the common wire 108 and to the lead wire 310 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
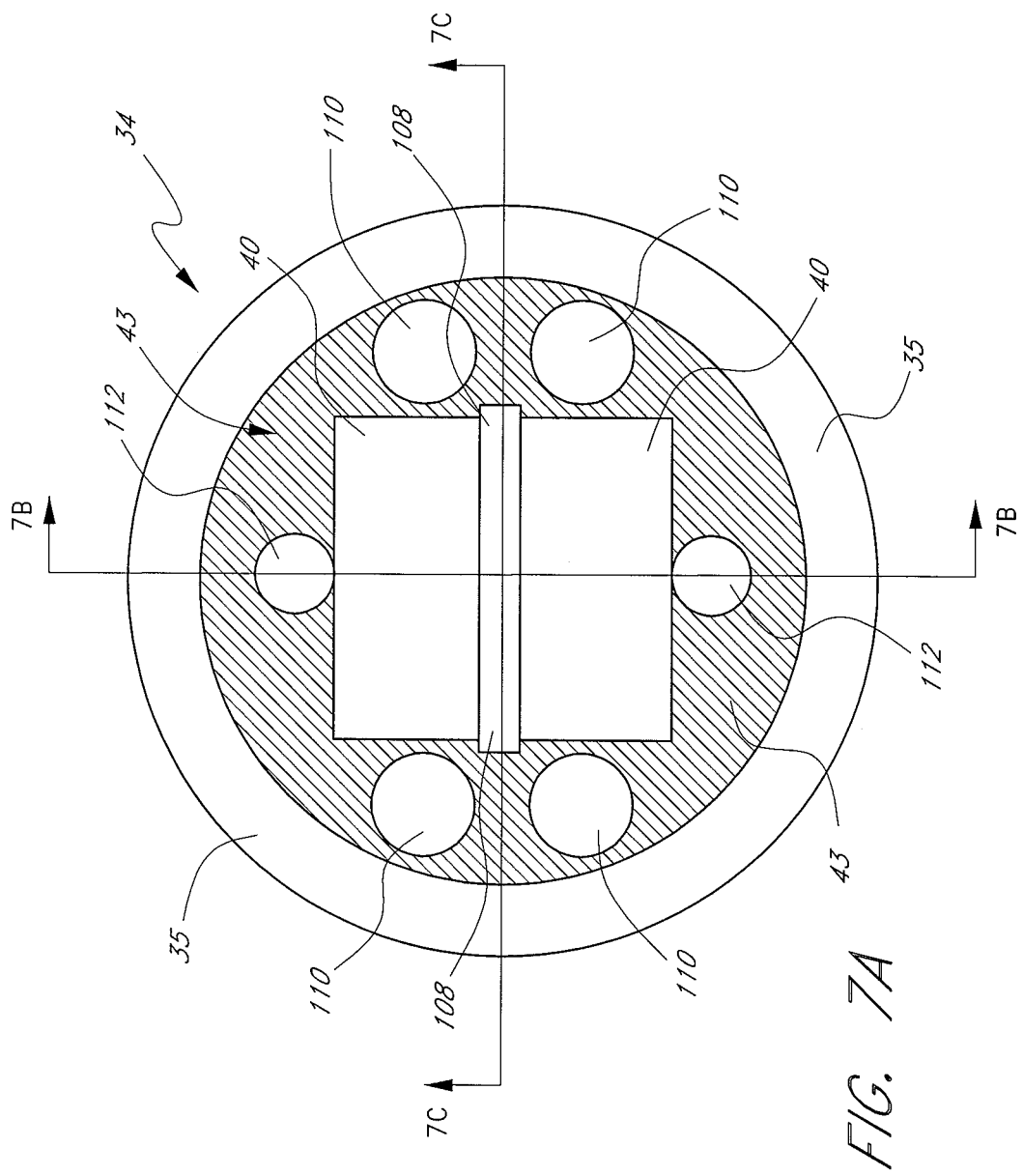
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 310 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 312. Because the common wire 108 is connected to the negative terminal 106, and the positive contact wire 312 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
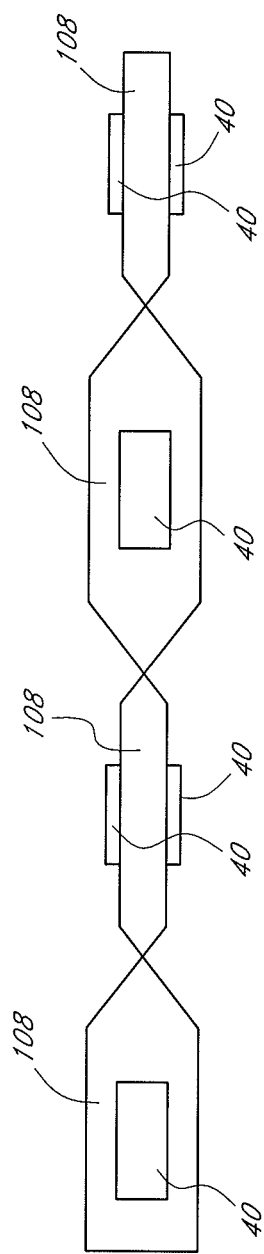
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focused, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configuration may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36 gauge electrical conductors, while positive contact wires 112 are preferably 42 gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment 1 MHz and 3 MHz. In yet another embodiment, the ultrasound radiating members 40 are operated with a frequency of about 2 MHz.

Figure 8:
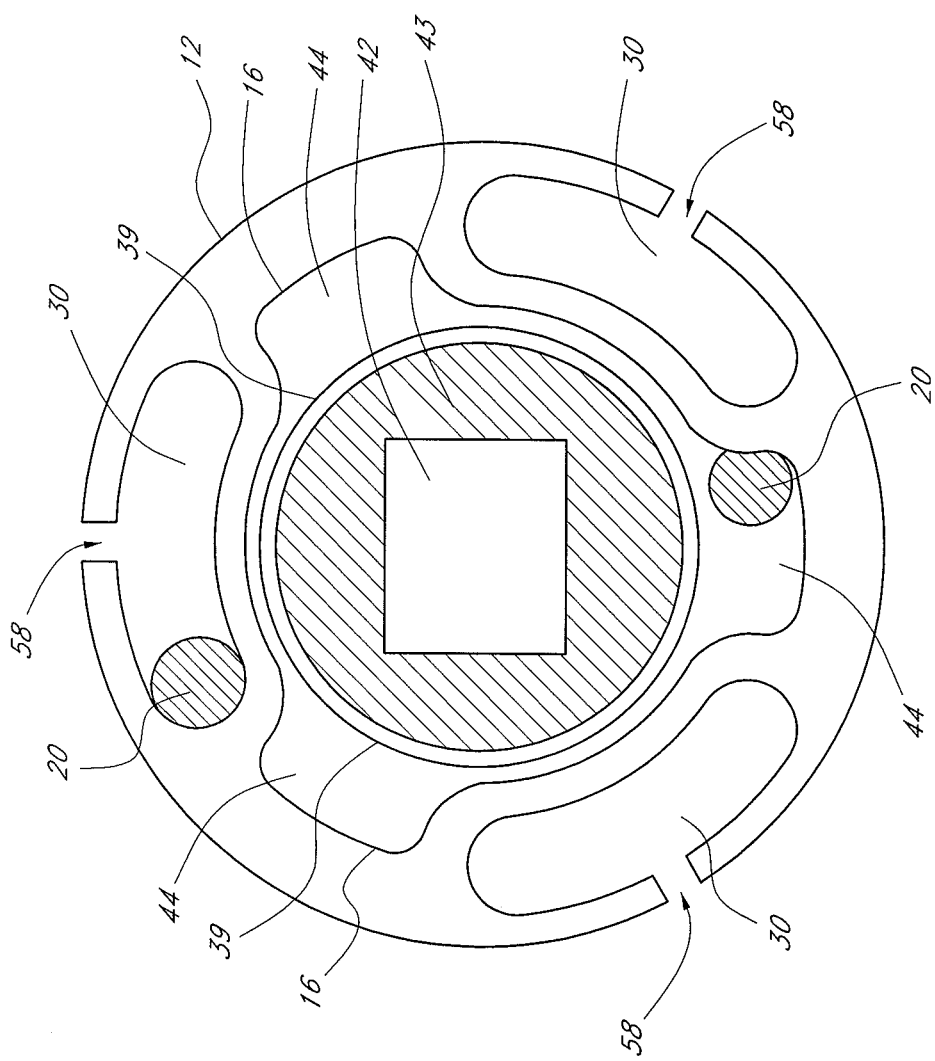
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters then fluid delivery closer to the distal region of the energy delivery section 18, thereby allowing uniform delivery of fluid across the entire energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid can is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120.degree. increments for a three-lumen configuration), thereby providing uniform cooling fluid flow over the inner core 34. Such a configuration is desirably to remove unwanted thermal energy at the treatment site. As will be explained below, the flow rate of the cooling fluid and the power to the ultrasound assembly 42 can be adjusted to maintain the temp of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by making providing the inner core 34 with a length that is less than the length of the tubular body. In other embodiments, a protrusion is formed on the internal side of the tubular body in the distal region 15, thereby preventing the inner core 34 from passing through the distal exit port.

In still other embodiments, the catheter 10 further comprises an occlusion device (not shown) positioned at the distal exit port 29. The occlusion device preferably has a reduced inner diameter that can accommodate a guidewire, but that is less than the inner diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30 (as illustrated), and/or within one or more of the cooling fluid lumens 44.

Figure 9:
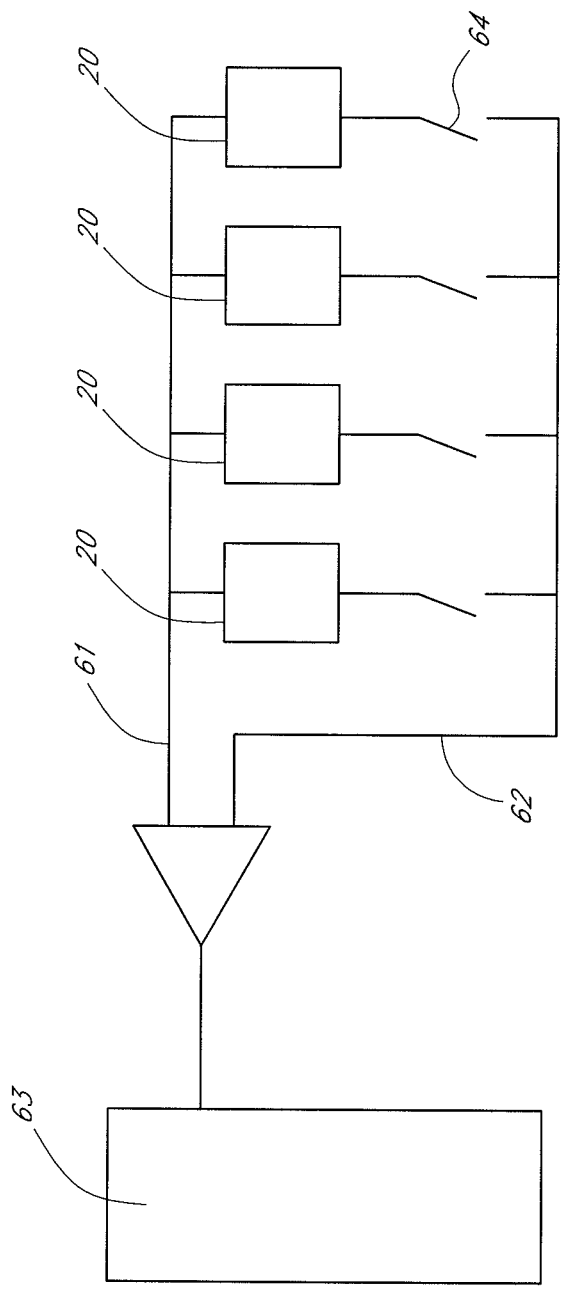
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2 n wires through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
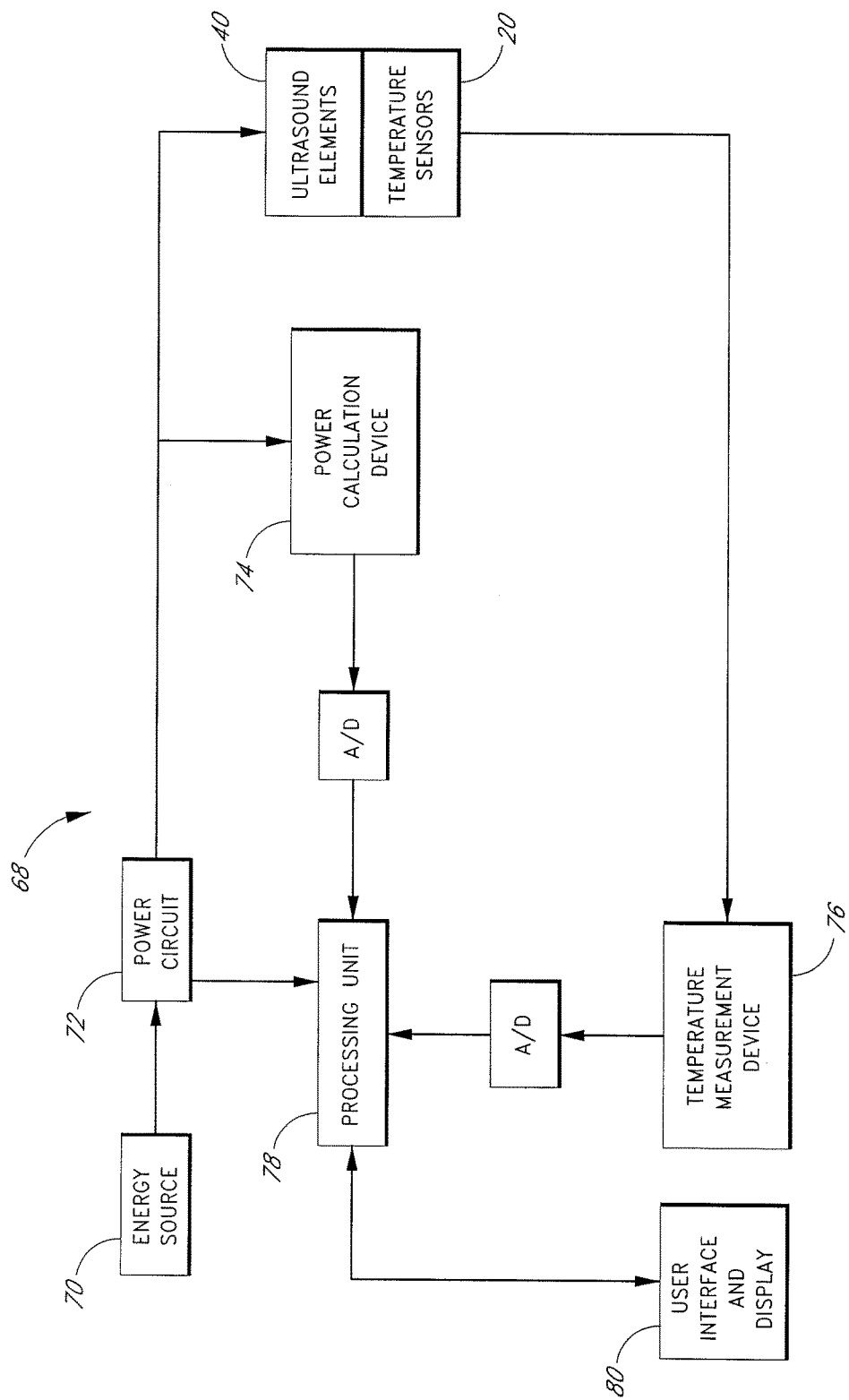
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system 1100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (at set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6.degree. C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members are preferably operated in a pulsed mode. For example, in one embodiment, the time average electrical power supplied to the ultrasound radiating members is between about 0.001 watts and 5 watts and can be between about 0.05 watts and 3 watts. In certain embodiments, the time average electrical power over treatment time is approximately 0.45 watts or 1.2 watts. The duty cycle is between about 0.01% and 90% and can be between about 0.1% and 50%. In certain embodiments, the duty ratio is approximately 7.5%, 15% or a variation between 1% to 30%. The pulse averaged electrical power can be between about 0.01 watts and 20 watts and can be between approximately 0.1 watts and 20 watts. In certain embodiments, the pulse averaged electrical power is approximately 4 watts, 8 watts, 16 watts, or a variation of 1 to 8 watts. As will be described above, the amplitude, pulse width, pulse repetition frequency, average acoustic pressure or any combination of these parameters can be constant or varied during each pulse or over a set of portions. In a non-linear application of acoustic parameters the above ranges can change significantly. Accordingly, the overall time average electrical power over treatment time may stay the same but not real-time average power.

In one embodiment, the pulse repetition rate is preferably between about 1 Hz and 2 kHz and more can be between about 1 Hz and 50 Hz. In certain preferred embodiments, the pulse repetition rate is approximately 30 Hz, or a variation of 10 to 40 Hz. The pulse duration or width is can be between about 0.5 millisecond and 50 milliseconds and can be between about 0.1 millisecond and 25 milliseconds. In certain embodiments, the pulse duration is approximately 2.5 milliseconds, 5 or a variation of 1 to 8 milliseconds. In addition, the average acoustic pressure can be between about 0.1 to 2 MPa or in another embodiment between about 0.5 or 0.74 to 1.7 MPa.

In one particular embodiment, the transducers are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating member used with the electrical parameters described herein preferably has an acoustic efficiency than 50% and can be greater than 75%. The ultrasound radiating member can be formed a variety of shapes, such as, cylindrical (solid or hollow), flat, bar, triangular, and the like. The length of the ultrasound radiating member is preferably between about 0.1 cm and about 0.5 cm. The thickness or diameter of the ultrasound radiating members is preferably between about 0.02 cm and about 0.2 cm.

Figure 11:
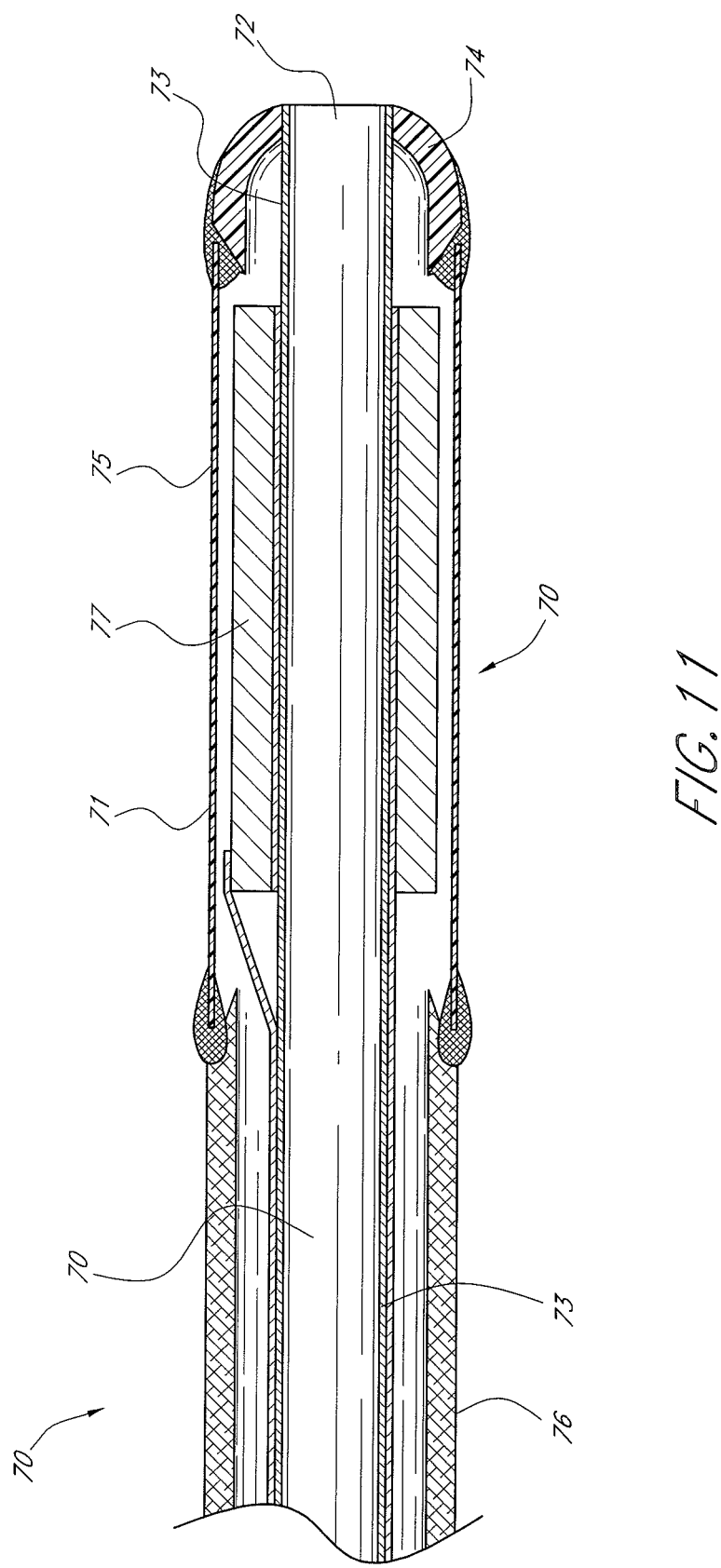
FIG. 11 is a longitudinal cross-sectional view of selected components of an exemplary ultrasound catheter assembly that is particularly well-suited for treatment of cerebral vascular occlusions, and that includes a cavitation promoting surface.

With reference now to FIG. 11, the energy delivery section of an ultrasound catheter that is configured for treating small vessels (e.g., for treatment of cerebral vascular occlusions) is shown and that includes an optional cavitation promoting surface 71. In this embodiment, the catheter includes an inner core 73 that defines a utility lumen 72 configured to pass materials such as a guidewire, a therapeutic compound and/or a cooling fluid. The catheter assembly 70 further includes a distal tip element 74 and a hollow cylindrical ultrasound radiating member 77 that is mounted on the inner core 73. Certain of these components are optional, and are omitted from alternative embodiments. In an example embodiment, the diameter of the catheter outer body 76 is less than about 5 French, although other dimensions are used in other embodiments. In addition, although only a single ultrasound element is shown, in modified embodiments, more one ultrasound element can b mounted along the lumen 72.

In example embodiments, the ultrasound radiating member 77 illustrated in FIG. 11s a tubular piezoceramic transducer that is able to radiate ultrasonic energy in a length mode, a thickness mode, and a circumferential mode. The ultrasound radiating member 77 is capable of generating a peak acoustic pressures that are preferably between about 0.7 MPa and about 10 MPa, and that are more preferably between about 1.2 MPa and about 6 MPa. However such parameters may be different if the catheter includes cavitation promoting surfaces or other modifications.

In a modified embodiment, the ultrasound radiating member 77 has a resonant frequency greater than or equal to approximately 1 MHz in the thickness mode. In certain embodiments, the ultrasound radiating member included in an ultrasound catheter optionally includes an electrode, such as a nickel-plated electrode, that enables electrical wires to be soldered thereto.

As will be described below, the ultrasound catheter includes one or more one or more ultrasound radiating members positioned therein. Such ultrasound radiating members can comprise a transducer (e.g., a PZT transducer), which is configured to convert electrically energy into ultrasonic energy. In such embodiments, the PZT transducer is excited by specific electrical parameters (herein "power parameters" or "acoustic parameters" that cause it to vibrate in a way that generates ultrasonic energy). As will be explained below, Applicants have discovered that non-linearly varying (e.g., randomly or pseudo randomly) one or more of the power parameters the effectiveness of the ultrasound catheter (e.g., the effectiveness of enhancing the removal of a thrombus) can be significantly enhanced. By non-linearly varying one or more of the power parameters the ultrasound radiating members create nonlinear acoustic pressure, which as described above can increase the effectiveness of the acoustic pressure in enhancing a therapeutic compound. In one application, the effect of nonlinearly varying acoustic pressure has been found by Applicant to enhance enzyme medicated thrombolysis by almost 1.9 times as compared to the application of substantially constant acoustic pressure. Examples of nonlinear variances include, but are not limited to, multi variable variations, variations as a function of a complex equation, sinusoidal variations, exponential variations, random variations, pseudo random variations and/or arbitrary variations. While nonlinear variance is preferred, in other arrangements it is anticipate that one or more of the parameters discussed can be varied in a linear manner either alone or combination with the nonlinear variance.

Figure 12:
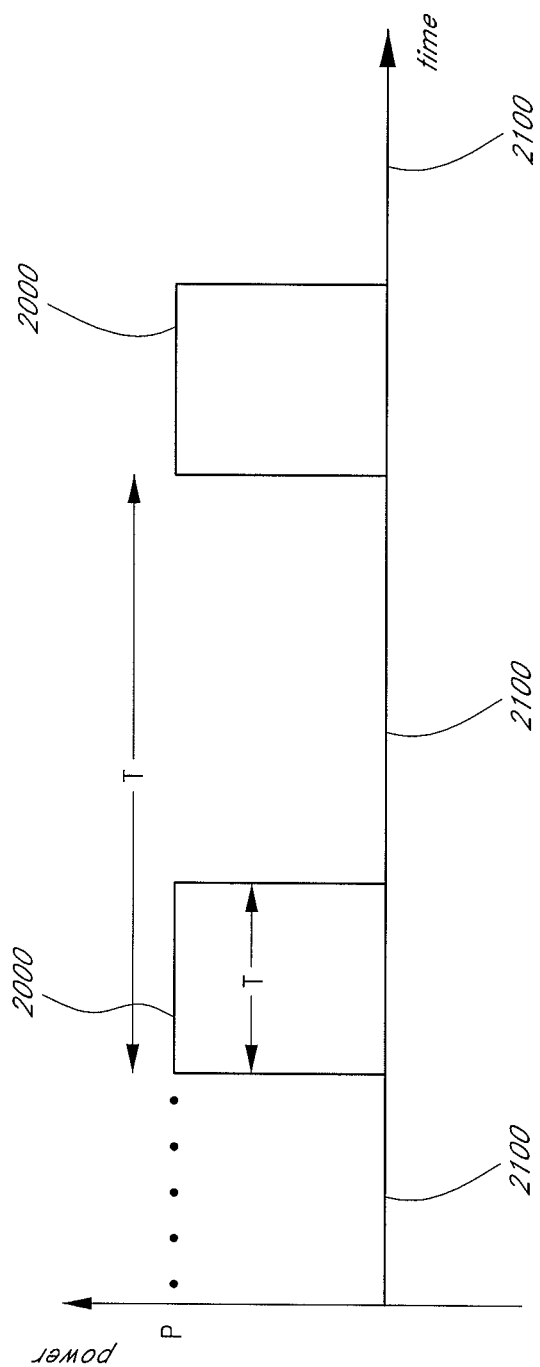
FIG. 12 schematically illustrates an example ultrasonic energy pulse profile.

FIG. 12 will be used to explain certain power parameters which can used to drive the ultrasound radiating members. As shown, the members can be driven a series of pulses 2000 having peak power P or amplitude and duration τ. During these pulses 2000, the ultrasound radiating members as driven at a certain frequency f as described above by the electrical current. The pulses 2000 can be separated by "off"

periods 2100. The cycle period T is defined as the time between pulse initiations, and thus the pulse repetition frequency ("PRF") is given by $T^{-1}$. The duty cycle is defined as the ratio of time of one pulse to the time between pulse initiations $\tau T^{-1}$, and represents the fraction of time that ultrasonic energy is being delivered to the treatment site. The average power delivered in each cycle period is given by $P\tau T^{-1}$. Accordingly, the illustrated embodiment, the ultrasound radiating members are operated using pulses, or modulated electrical drive power instead of continuous drive power In one embodiment, the average power delivered in each cycle period is preferably between about 0.1 watts and about 2.0 watts. In a such an embodiment, each cycle period has a different average power value, wherein the average power values for the different cycles vary in a nonlinear fashion. Examples of non-linear variation include, but are not limited to, simple or complex variable or multi-variable equations, varying randomly, pseudo randomly and/or in an arbitrary manner. For instance, in one such modified embodiment, each cycle period has an average power quantity that is randomly or pseudo randomly distributed between a maximum average power quantity and a minimum average power quantity. The average power of each cycle period can be adjusted by manipulating one or more parameters of the waveform in the cycle period, such as, but not limited to, peak power P, reduced power P', pulse repetition frequency, pulse duration $\tau$, and duty cycle.

In another embodiment, the duty cycle is preferably between about 1% and about 50%, is more preferably between about 2% and about 28%. During operation of the catheter, the duty cycle can vary in a nonlinear fashion. For instance, in one such modified embodiment, the duty cycle that is randomly or pseudo randomly distributed between a maximum duty cycle and a minimum duty cycle. For example, in one embodiment, the values for the maximum duty cycle are between about 25% and about 30%, and typical values for the minimum duty cycle are between about 1.5% and about 3.5%. In yet another embodiment, the duty cycle is varied non-linearly from a minimum value of 2.3% and a maximum value of 27.3%. In one embodiment, other parameters of the waveform are manipulated such that each cycle period has the same average power, even though the duty cycle for each cycle period is varying in a nonlinear fashion.

In another embodiment, the peak power P delivered to the treatment site is preferably between about 0.1 watts and about 20 watts, is more preferably between about 5 watts and about 20 watts, and is most preferably between about 8 watts and about 16 watts. Within the ranges, during operation of the catheter, the peak power P can vary in a nonlinear fashion. For instance, in one such modified embodiment, each cycle period has a peak power quantity that is randomly or pseudo randomly distributed between a maximum peak power $P_{max}$ and a minimum peak power $P_{min}$. Typical values for the maximum peak power $P_{max}$ are between about 6.8 watts and about 8.8 watts, and typical values for the minimum peak power $P_{min}$ are between about 0.1 watts and about 1.0 watts. In another embodiment, the peak power is varied non-linearly between a maximum peak power $P_{max}$ of 7.8 watts and a minimum peak power $P_{min}$ of 0.5 watts. In one embodiment, other parameters of the waveform are manipulated such that each cycle period has the same average power, even though the peak power P for each cycle period is varying in a nonlinear fashion.

In another embodiment, the effect of a therapeutic compound is optionally enhanced by using a certain pulse repetition frequency PRF and/or a certain pulse duration $\tau$. In one example embodiment, the PRF is preferably between about 5 Hz and about 150 Hz, is more preferably between about 10 Hz and about 50 Hz, and is most preferably between about 20 Hz and about 40 Hz. In one embodiment, the PRF remains substantially constant during the course of a treatment. However, in certain modified embodiments the PRF is non-linearly varied during the course of a treatment within the ranges described above. For example, in one such modified embodiment the PRF is varied linearly during the course of the treatment, while in another such modified embodiment the PRF is varied nonlinearly during the course of the treatment. Examples of nonlinear variances include, but are not limited to, sinusoidal variations, exponential variations, and random variations. For instance, in an example embodiment the PRF is varied randomly between a maximum PRF and a minimum PRF during the course of a treatment. Typical values for the maximum PRF are between about 28 Hz and about 48 Hz, and typical values for the minimum PRF are between about 5 Hz and about 15 Hz. In another embodiment, the maximum PRF is about 38 Hz and the minimum is about 10 Hz. In one embodiment, the pulse repetition interval is varied between about 25 to about 100 ms.

The pulse amplitude, pulse width and pulse repetition frequency during each pulse can also be constant or varied in a non-linear fashion as described herein. Other parameters are used in other embodiments depending on the particular application.

In one example embodiment, the pulse duration $\tau$ is preferably between about 1 millisecond and about 50 milliseconds, is more preferably between about 1 millisecond and about 25 milliseconds, and is most preferably between about 2.5 milliseconds and about 5 milliseconds. In a modified embodiment, each cycle period has a different pulse duration $\tau$, wherein the pulse duration values vary in a nonlinear fashion with the ranges described above. For instance, in one such modified embodiment, each cycle period has a pulse duration quantity that is randomly distributed between a maximum pulse duration $\tau_{max}$ and a minimum pulse duration $\tau_{min}$. Typical values for the maximum pulse duration $\tau_{max}$ are between about 6 milliseconds and about 10 milliseconds (and in one embodiment 8 milliseconds), and typical values for the minimum pulse duration $\tau_{min}$ are between about 0.1 milliseconds and about 2.0 milliseconds (and in one embodiment 1 millisecond), In one embodiment, other parameters of the waveform are manipulated such that each cycle period has the same average power, even though the pulse duration $\tau$ for each cycle period is varying in a nonlinear fashion. In other embodiments, the average power can be varied non-linearly.

In addition, the average acoustic pressure can also non-linearly varied as described above between about 0.1 to 2 MPa or in another embodiment between about 0.5 or 0.74 to 1.7 MPa.

The control system 1100 can be configured to vary one or more of the power parameters as discussed above. Accordingly, the control system 1100 can include any of a variety of control routines, control circuits, etc. so as to vary the power parameters described above. As mentioned above, the control parameters can be varied in combination with other operating parameters (e.g., frequency) of the ultrasound radiating member and/or catheter. Alternatively, the power parameters may be varied using a software package that controls the operation of the ultrasound radiating members. It should also be appreciated that one, two, three or all of the parameters (and subsets thereof) can be non-linearly varied at the same time or by themselves.

A study to investigate the effect of a variety of randomization protocols on clot lysis was conducted. The randomization protocols involved non-linearly varying peak power, pulse width, pulse repetition frequency, or combinations of the above. The randomization protocols were tested using a time average power of either 0.45 W or 0.90 W, and were compared to a standard Neurowave E11 protocol.

Clots were prepared by adding 1 mL of citrated human pooled plasma to a polystyrene culture tube. Clotting was initiated by the addition of 100 μL of 0.2 M calcium chloride and 100 μL of 12.5 U/ml bovine thrombin. Fixtures equipped with drug delivery lumens and an ultrasonic catheter were inserted into the clot, thereby allowing the clot to form around the fixtures. Clots were allowed to incubate for 10 minutes in a 37 degrees C. water bath before initiating the clot lysis procedure.

Clot lysis was initiated by delivering rt-PA to the clot via the drug delivery lumens. A total of 0.08 mL of 5000 U/mL rt-PA solution was delivered to the clot over a period of 5 minutes at a rate of 0.96 mL/hr.

After drug delivery was completed, the clot was subjected to 5 minutes of ultrasound exposure, and 25 minutes of additional incubation time subsequent to the ultrasound treatment. The clots were then removed from the polystyrene culture tubes and pressed between filter paper to remove serum from the clots before the clots were weighed.

The acoustic protocols tested are summarized in Table 1 provided below. "PW" represents pulse width and "PRF" represents pulse repetition frequency. Ranges indicate that the parameter was varied randomly within the range shown. For example, for the R3P-d protocol, peak power was varied from 1.6 to 7.9 W, pulse width was varied from 1.16 to 8.16 ms, and pulse repetition frequency was varied from 10 to 40 Hz.

TABLE 1

Description of acoustic protocols

| Acoustic Protocol | Average Power | Peak Power | PW | PRF |
|---|---|---|---|---|
| Neurowave E11 (E11-S) | 0.45 W | 5.3 W | 2.8 ms | 30 Hz |
| R3P-d (R1.4) | 0.45 W | 1.6-7.9 W | 1.16-8.16 ms | 10-40 Hz |
| R1P-f (R5.5) | 0.45 W | 3.75 W | 0.31-19.53 ms | 30 Hz |
| R1P-g (R5.6) | 0.90 W | 3.75 W | 0.62-39.07 ms | 30 Hz |
| R2P-a (R6.0) | 0.45 W | 1.6-7.9 W | 0.54-9.8 ms | 30 Hz |
| R2P-b (R6.1) | 0.90 W | 1.6-7.9 W | 1.09-19.6 ms | 30 Hz |

The randomization protocols were compared to the fixed parameter Neurowave E11 protocol as described in Table 1. Lysis enhancement factor (LEF %) was calculated using the following formula:

$$LEF\% = \left(\left(\frac{W_c - W_{lus_i}}{W_c - W_l}\right) - 1\right) \times 100$$

The variables in the above equation are:
$W_c$[mg]: Average clot weight of the negative control samples (no treatment).
$W_l$[mg]: Average clot weight from positive control group (drug treatment only).
$W_{lus}$[mg]: Average clot weight from each individual ultrasound treatment group.

Figure 13:
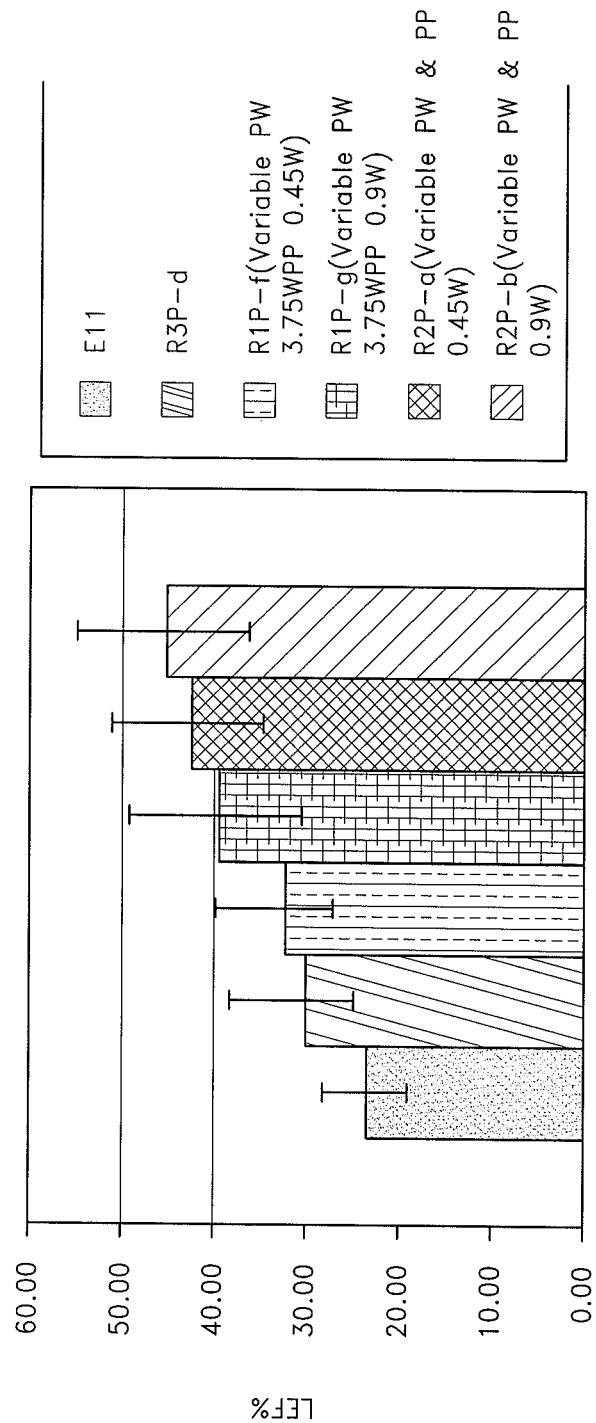
FIG. 13 is a chart showing the lysis enhancement factor of a variety of ultrasonic protocols.

FIG. 13 shows the LEF % for the protocols tested. The results indicate that varying peak power and pulse width simultaneously in the randomization protocol give significantly better lysis enhancement in the test environment than varying either parameter alone or when they are varied together with pulse repetition frequency. In addition, higher peak powers generally yielded improved lysis response. It should be appreciated that the Lysis enhancement factor is only one measure of the efficacy of the treatment and that the methods and technique described above may have additional and/or different efficacy benefits in situ.

In one embodiment, one way of implementing a randomization protocol is to generate and execute a plurality of ultrasonic cycle profiles, where each ultrasonic cycle profile can have randomly generated power parameter values. As previously mentioned, power parameters include, but are not limited to, peak power, pulse width, pulse repetition frequency and pulse repetition interval. Generally, for each power parameter, a random number generator, for example, can be used to select a value within a bounded range determined by the operator. Examples of suitable ranges are described above. For example, one ultrasonic cycle profile can have a randomly selected peak power value, while the other power parameters are non-randomly selected. Another ultrasonic cycle profile may have a plurality of randomly selected power parameters values, such as peak power and pulse width. This process can be used to generate the desired number of ultrasonic cycle profiles.

Each ultrasonic cycle profile can be run for a profile execution time. For example, if the profile execution time is approximately 5 seconds, each ultrasonic cycle profile will be run for approximately 5 seconds before the next ultrasonic cycle profile is run. In some embodiments, the profile execution time is less than about 5 seconds. For example, in some embodiments the profile execution time is between about one second and about 30 seconds. In some embodiments, the profile execution time is less than about one second. In some embodiments, the profile execution time is increased so that accurate measurements can be taken of the executed power parameters. In some embodiments, the profile execution time itself can be selected randomly from a predetermined range.

In some embodiments, it is desirable to deliver a particular time averaged power. Because the power parameters may be randomized, it may take the execution of a plurality of ultrasonic cycle profiles before the time averaged power approaches an asymptotic value. In some embodiments, the execution of about 40 to 50 ultrasonic cycle profiles is required for the time averaged power to become asymptotic. In other embodiments, less than about 40 ultrasonic cycle profiles are required, while in yet other embodiments, more than about 50 ultrasonic cycle profiles are required. In some embodiments, ultrasonic cycle profiles are executed until the time average power approaches an asymptotic value. For example, if the profile execution time is 5 seconds and the overall execution time is 30 minutes, 360 ultrasonic cycle profiles will be executed, which in some embodiments is sufficient for the time average power to approach an asymptotic value.

In addition, although many embodiments have been described in the context of an intravascular catheter it should be appreciated that the non-linear application of one or more power parameters can also be applied to non-intravascular catheters or devices and/or non catheter applications. For example, the non-linear varying of one or more power parameters may also find utility in applications in which the ultrasound is applied through an external (with respect to the body or with respect to the vascular system). In particular, the discussion above can be applied to external ultrasound application in which the ultrasound source is external to the patient and/or treatment site. It is also anticipated that the methods and techniques described herein can be applied to non-vascular applications. In addition, in some embodiments, the therapeutic affects of the ultrasound can be utilized alone without a therapeutic compound.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than treatment of vascular occlusions.

What is claimed is:

1. A method of operating an ultrasonic catheter comprising:
    advancing a catheter with at least one ultrasonic element to a treatment site in a patient's vascular system;
    driving the at least one ultrasonic element to generate ultrasonic energy;
    delivering a therapeutic compound to the treatment site through the catheter; and
    non-linearly varying a power parameter of the at least one ultrasonic element, wherein the power parameter is selected from the group consisting of peak power, pulse repetition frequency, pulse width, and pulse repetition interval,
    wherein the peak power is randomly or pseudo randomly distributed between a bounded maximum peak power $P_{max}$ and a bounded minimum peak power $P_{min}$,
    wherein the pulse repetition frequency is varied randomly between a bounded maximum pulse repetition frequency and a bounded minimum pulse repetition frequency,
    wherein the pulse width is varied randomly within a bounded range, and
    wherein the pulse repetition interval is varied randomly within a bounded range.

2. The method of claim 1, wherein the power parameter is the peak power.

3. The method of claim 1, wherein the treatment site includes a vascular occlusion.

4. The method of claim 1, wherein the therapeutic compound comprises a thrombolytic agent.

5. A method of delivering ultrasound to a patient comprising:
    advancing a catheter with at least one ultrasonic element to a treatment site in a patient's vascular system;
    driving the at least one ultrasonic element to generate ultrasonic energy; and
    non-linearly varying a power parameter of the at least one ultrasonic element, wherein the power parameter is selected from the group consisting of peak power, pulse repetition frequency, pulse width, and pulse repetition interval,
    wherein the peak power is randomly or pseudo randomly distributed between a bounded maximum peak power $P_{max}$ and a bounded minimum peak power $P_{min}$,
    wherein the pulse repetition frequency is varied randomly between a bounded maximum pulse repetition frequency and a bounded minimum pulse repetition frequency,
    wherein the pulse width is varied randomly within a bounded range,
    wherein the pulse repetition interval is varied randomly within a bounded range, and
    wherein the non-linearly varying is performed by a control system.

6. The method of claim 5, wherein the power parameter is the peak power.

7. The method of claim 5, further comprising delivering a therapeutic compound to the patient.

* * * * *